United States Patent
Woehrle et al.

(10) Patent No.: US 12,138,024 B2
(45) Date of Patent: Nov. 12, 2024

(54) INFLATION APPARATUS FOR AN INFLATION-BASED NON-INVASIVE BLOOD PRESSURE MONITOR AND A METHOD OF OPERATING THE SAME

(71) Applicant: KONINKLIJKE PHILIPS N.V., Eindhoven (NL)

(72) Inventors: Dieter Woehrle, Waiblingen (DE); Lars Schmitt, Aachen (DE); Maarten Petrus Joseph Kuenen, Veldhoven (NL); Paul Aelen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 780 days.

(21) Appl. No.: 16/647,363

(22) PCT Filed: Sep. 11, 2018

(86) PCT No.: PCT/EP2018/074435
§ 371 (c)(1),
(2) Date: Mar. 13, 2020

(87) PCT Pub. No.: WO2019/052996
PCT Pub. Date: Mar. 21, 2019

(65) Prior Publication Data
US 2020/0275847 A1    Sep. 3, 2020

(51) Int. Cl.
*A61B 5/022*    (2006.01)
*A61B 5/0225*    (2006.01)
*A61B 5/0235*    (2006.01)

(52) U.S. Cl.
CPC ...... *A61B 5/02233* (2013.01); *A61B 5/02208* (2013.01); *A61B 5/02225* (2013.01); *A61B 5/0225* (2013.01); *A61B 5/0235* (2013.01)

(58) Field of Classification Search
CPC ............ A61B 5/02233; A61B 5/02208; A61B 5/02225; A61B 5/0225; A61B 5/0235; A61B 5/022; A61B 5/02141
See application file for complete search history.

(56) References Cited

U.S. PATENT DOCUMENTS

| | | | |
|---|---|---|---|
| 5,261,413 A | 11/1993 | Kawahara | |
| 5,517,999 A | 5/1996 | Newell | |

(Continued)

FOREIGN PATENT DOCUMENTS

| | | |
|---|---|---|
| CN | 104696186 A | 6/2015 |
| CN | 204394491 U | 6/2015 |

(Continued)

OTHER PUBLICATIONS

English Machine Translation of Tsukuda (WO-2013046556-A1) (Year: 2013).*

(Continued)

*Primary Examiner* — Jay B Shah

(57) ABSTRACT

According to an aspect there is provided an inflation apparatus (10) for use in an inflation-based non-invasive blood pressure, NIBP, measurement apparatus, the inflation apparatus comprising: an outlet (110) configured to be coupled to a cuff of the inflation-based NIBP measurement apparatus; a plurality of pumps (120) each configured to output a flow of gas to the outlet; and a control unit (130) configured to enable at least one of the plurality of pumps to output a flow of gas to the outlet based on a required flow rate to inflate the cuff and/or to control a flow rate of at least one of the plurality of pumps to output a flow of gas to the outlet based on a required flow rate to inflate the cuff.

18 Claims, 7 Drawing Sheets

(56) References Cited

U.S. PATENT DOCUMENTS

| | | |
|---|---|---|
| 2006/0074325 A1* | 4/2006 | Karo ............... A61B 5/022 600/494 |
| 2011/0152650 A1 | 6/2011 | Donehoo et al. |
| 2012/0330112 A1 | 12/2012 | Lamego et al. |
| 2013/0226138 A1 | 8/2013 | Sia |
| 2014/0316290 A1 | 10/2014 | Kobayashi et al. |
| 2017/0245769 A1 | 8/2017 | Niehaus et al. |
| 2018/0023548 A1 | 1/2018 | Øllgaard |
| 2019/0343405 A1* | 11/2019 | Tanaka ............... F04B 45/047 |

FOREIGN PATENT DOCUMENTS

| | | | |
|---|---|---|---|
| JP | 2008228916 A * | 10/2008 | ........... A61B 5/0225 |
| JP | 2011083496 A | 4/2011 | |
| JP | 2014014556 A * | 1/2014 | |
| WO | WO-2006124768 A1 * | 11/2006 | ......... A61B 5/02208 |
| WO | 2011158479 A1 | 12/2011 | |
| WO | WO-2013046556 A1 * | 4/2013 | ......... A61B 5/02225 |
| WO | 2016030232 A1 | 3/2016 | |
| WO | 2019052918 A1 | 9/2018 | |

OTHER PUBLICATIONS

English Machine Translation of Sawanoi (JP 2014014556) (Year: 2014).*

International Search Report and Written Opinion, International Application No. PCT/EP2018/074435, Mailed on Nov. 7, 2018.

Nihon Kohden, https://www.nihonkohden.com/, Accessed Mar. 11, 2020.

Welch Allyn, "Connex® ProBP™ 3400 Digital Blood Pressure Device", 2014.

* cited by examiner

INFLATION APPARATUS FOR AN INFLATION-BASED NON-INVASIVE BLOOD PRESSURE MONITOR AND A METHOD OF OPERATING THE SAME

This application is the U.S. National Phase application under 35 U.S.C. § 371 of International Application No. PCT/EP2018/074435, filed on 11 Sep. 2018, which claims the benefit of European Application Serial No. 17191108.4, filed 14 Sep. 2017. These applications are hereby incorporated by reference herein.

FIELD OF THE INVENTION

The invention relates to an inflation apparatus for an inflation-based non-invasive blood pressure measurement apparatus and a method of operating the same, and in particular relates to providing an inflation apparatus that is suitable for use with a large range of different inflatable cuffs varying in sizes and materials.

BACKGROUND TO THE INVENTION

Arterial blood pressure (BP) is one of the most important vital signs and is widely used in clinical practice. Non-invasive arterial blood pressure (NIBP) is usually measured by slowly varying the pressure in a cuff that is wrapped around an upper arm of a subject. The BP is determined either by measuring sound distal from the cuff (the auscultatory method, based on Korotkoff sounds) or by measuring pressure pulsations in the cuff caused by volume pulsations of the arm and brachial artery and extracting features from the envelope of these pressure pulses (the oscillometric method). The oscillometric method is easily automated and is widely used.

The principle behind a typical auscultatory or oscillometric method is illustrated by FIG. 1 and FIG. 2, which show respectively pressure applied to the cuff versus time and pressure measured at the inflatable cuff versus time. The y-axis shows cuff pressure, and the x-axis shows time.

To perform a deflation based NIBP measurement using either the auscultatory method or the oscillometric method, a cuff is inflated around the upper arm of a subject until all blood flow is occluded. Subsequently, the cuff pressure is slowly decreased stepwise as shown in FIG. 1, or linearly in other types of measurement techniques. Signals measured during the decrease of cuff pressure are then used to determine systolic blood pressure (SBP, i.e. maximum blood pressure during the heart cycle) and diastolic blood pressure (DBP, i.e. minimum blood pressure during the heart cycle). During this process, the subject, e.g. a patient, is likely to experience discomfort and this is represented by the area under the line in FIG. 1. The product of time and pressure results in a level of discomfort—in other words, a high pressure for a long time is uncomfortable for the subject, and a lower pressure could also result in the same level of the discomfort if applied for a longer period.

As illustrated in FIG. 2, in the auscultatory method, SBP and DBP are determined from the onset and disappearance of the Korotkoff sounds, which can be heard using a stethoscope placed over the brachial artery distal to the cuff by a healthcare professional. In the oscillometric method, SBP and DBP are determined from the cuff pressure oscillations that are observed. The amplitude of these oscillations is the largest when the cuff pressure is close to the mean arterial blood pressure. SBP and DBP are typically determined as the cuff pressure where the oscillation amplitude is within a specific percentage range (characteristic ratio) of the peak oscillation amplitude. Common characteristic ratios are around 70% to 80% for DBP and around 50% to 60% for SBP.

One of the problems with deflation-based techniques such as the one described above is the discomfort introduced to the subject (represented by the area under the line in FIG. 1). Pressures above a certain level can cause discomfort and even pain, either due to the pressure exerted by the cuff itself or due to the build-up of venous blood (venous pooling) in the part of the limb distal to the cuff. The longer these pressures are applied to the subject, the more discomfort is caused to the subject.

Another problem with deflation-based NIBP measurements is the long duration of the measurement itself. Deflation-based NIBP measurements typically take around 40 seconds to complete a single measurement. This duration can be perceived as too long by the subject (e.g. a patient) due to the discomfort caused by the pressure level, and it can also affect the workflow of medical personnel, who usually carry out blood pressure measurements for multiple patients. Moreover, the inherent variability of blood pressure over time can distort a blood pressure measurement during deflation of the cuff.

The comfort of the NIBP measurement can be improved in any or all of three areas: the total measurement time (where a reduction is desired), the maximum cuff pressure reached (where a lower maximum pressure is desired), and the integral of cuff pressure over time (where a smaller integral is desired). Of course, this increase in comfort should not come at the expense of the accuracy of the NIBP measurement beyond acceptable limits.

In addition to the types of measurement techniques described above in which the BP is measured during deflation of the cuff, apparatuses have been developed that can measure the BP while the cuff is being inflated. This can reduce the total measurement time (in some cases to around 20 seconds), since deflation can occur relatively quickly once the BP measurement has been obtained, and therefore can result in a measurement that is more comfortable for the subject (as shown by the dotted line in FIG. 1).

One existing measurement apparatus uses a fixed flow (i.e. fixed mL/s, variable mmHg/s) to inflate a cuff and another apparatus uses a fixed pressure rate (i.e. fixed mmHg/s, variable mL/s). The fixed flow solution results in a device only functional for a small range of cuffs, since the inflation may be too fast for smaller cuffs (i.e. too little number of oscillations to obtain an accurate estimate of SBP and DBP) and the measurement becomes slow for larger cuffs. The fixed pressure rate (i.e. a certain increase of pressure over a fixed period of time) solution addresses these issues by changing the flow for a certain desired pressure rate. However, a particular issue with this solution is that to be compatible for use with a large range of cuffs, a wide range of flows has to be generated and it is difficult for a normal pump to generate a wide range of flows which span the range from neonatal cuffs to thigh cuffs.

SUMMARY OF THE INVENTION

The use of a particular pump to inflate a blood pressure cuff might result in desired inflation rates for only a particular range of cuffs and/or other settings. That is, if a pump is chosen that can generate a high maximum flow, it might not be able to generate low flows in an accurate way. Particular issues might be related to not pumping at all (known as pump stalling) or inducing oscillations that are inseparable from the arterial oscillations that are to be measured to determine the blood pressure. On the other hand, if a pump is chosen that can deliver low flows, it might not be able to generate high flows. These issues result in blood pressure measurement devices that are only able to handle a certain range of cuff sizes; a pump with a large maximum flow might not be able to be used to obtain valid measurements for small cuffs and vice versa.

A further problem is that the use of a pump can induce unwanted oscillations in the signal of interest (i.e. the measurement of cuff oscillations that are induced by the artery). Particularly for low flows, these induced oscillations might be in the same frequency band as the arterial oscillations, which makes separation of these signals very difficult. This can result in artefacts in the desired signal which could make the blood pressure measurement less accurate, or even impossible to analyze.

One of the attempts to address the issues mentioned above is to use a gearbox to reduce the speed of the motor of the pump. A disadvantage of this approach is that a shift in gears in the gearbox may cause discontinuities in the inflation speed of the cuff which in turn may cause distortions of the oscillations at the cuff.

Therefore there is a need for an inflation apparatus for use in an inflation-based NIBP measurement apparatus and method of operating the same that addresses the issues discussed above and at the same time does not involve complex adaptations of existing pumps or elaborate controls.

According to a first aspect, there is provided an inflation apparatus for use in an inflation-based non-invasive blood pressure, NIBP, measurement apparatus, the inflation apparatus comprising: an outlet configured to be coupled to a cuff of the inflation-based NIBP measurement apparatus; a plurality of pumps each configured to output a flow of gas to the outlet; and a control unit configured to enable at least one of the plurality of pumps to output a flow of gas to the outlet based on a required flow rate to inflate the cuff and/or to control a flow rate of at least one of the plurality of pumps to output a flow of gas to the outlet based on a required flow rate to inflate the cuff.

In some embodiments, the required flow rate may be determined based on at least one of a rate of change of pressure at the cuff and a compliance value.

In some embodiments, the plurality of pumps may comprise a first pump configured to output a flow of gas within a first range of flow rates and a second pump configured to output a flow of gas within a second range of flow rates, wherein the first range may comprise higher flow rates than the second range, and wherein the control unit may be configured to enable one or both of the first pump and the second pump to provide a flow of gas from the enabled pump or pumps to the outlet at the required flow rate.

In some embodiments, enabling and/or disabling of at least one of the first pump and the second pump may be performed gradually.

In some embodiments, the first pump may be a diaphragm pump and the second pump may be a piezo pump.

In some embodiments, each of the plurality of pumps may be configured to output gas in a range of flow rates, and the control unit may be configured to enable at least one of the plurality of pumps to output a flow of gas and to control the flow rate of the at least one of the plurality of pumps to provide a flow of gas to the outlet at the required flow rate.

In some embodiments, the control unit may be configured to enable each of the plurality of pumps to provide a flow of gas to the outlet.

In some embodiments, the control unit may be configured to control each of the enabled pumps to output a flow of gas at the same or substantially the same flow rate.

In some embodiments, each of the plurality of pumps may be configured to output a flow of gas at a fixed flow rate, and the control unit may be configured to enable at least one of the plurality of pumps to provide a flow of gas from the enabled pumps to the outlet at the required flow rate.

In some embodiments, each of the plurality of pumps may output a flow of gas at the same or substantially the same fixed flow rate.

According to an aspect related to the first aspect, and applicable to any of the embodiments of the first aspect, there is provided an inflation apparatus for use in an inflation-based non-invasive blood pressure, NIBP, measurement apparatus, the inflation apparatus comprising an outlet configured to be coupled to a cuff of the inflation-based NIBP measurement apparatus; a plurality of pumps each configured to output a respective flow of gas to the outlet to produce a flow of gas at the outlet for inflating the cuff; and a control unit configured to (i) enable at least one of the plurality of pumps to output a respective flow of gas to the outlet, wherein the number of pumps enabled by the control unit is based on a required flow rate of gas at the outlet for inflating the cuff, and/or (ii) control at least one of the plurality of pumps to output a respective flow of gas to the outlet at a respective flow rate, wherein the respective flow rate of the at least one of the plurality of pumps is controlled based on the required flow rate.

According to a second aspect, there is provided an inflation-based non-invasive blood pressure NIBP measurement apparatus comprising: an inflation apparatus according to the first aspect or the aspect related to the first aspect, an inflatable cuff for placement around a body part of a subject, the inflatable cuff being coupled to the outlet of the inflation apparatus; and a sensor configured to measure arterial oscillations in the body part of the subject as the cuff is being inflated by the inflation apparatus; wherein the control unit of the inflation apparatus or a processing unit in the inflation-based NIBP measurement apparatus is configured to receive measurements of arterial oscillations from the sensor and to determine the blood pressure of the subject based on the received measurements.

In some embodiments, the inflation-based non-invasive blood pressure NIBP measurement apparatus may further comprise a release valve connected to the inflatable cuff for selectively deflating the cuff.

According to a third aspect, there is provided a method of controlling an inflation apparatus for use with an inflation-based non-invasive blood pressure NIBP measurement apparatus, the inflation apparatus comprising an outlet configured to be coupled to a cuff of the inflation-based NIBP measurement apparatus; a plurality of pumps each configured to output a flow of gas to the outlet, the method in a control unit of the control unit comprising: enabling at least one of the plurality of pumps to output a flow of gas to the outlet based on a required flow rate to inflate the cuff, and/or controlling a flow rate of at least one of the plurality of pumps to output a flow of gas to the outlet based on a required flow rate to inflate the cuff.

In some embodiments, the method may further comprise determining the required flow rate based on at least one of a rate of change of pressure at the cuff and a compliance value.

In some embodiments, the plurality of pumps may comprise a first pump configured to output a flow of gas within a first range of flow rates and a second pump configured to output a flow of gas within a second range of flow rates, wherein the first range may comprise higher flow rates than the second range, and the method may further comprise enabling one or both of the first pump and the second pump to provide a flow of gas from the enabled pump or pumps to the outlet at the required flow rate.

In some embodiments, the method may further comprise enabling and/or disabling of at least one of the first pump and the second pump gradually.

In some embodiments, each of the plurality of pumps may be configured to output gas in a range of flow rates, and the method may further comprise enabling at least one of the plurality of pumps to output a flow of gas and to control the flow rate of the at least one of the plurality of pumps to provide a flow of gas to the outlet at the required flow rate.

In some embodiments, the method may further comprise enabling each of the plurality of pumps to provide a flow of gas to the outlet.

In some embodiments, the method may further comprise controlling each of the enabled pumps to output a flow of gas at the same or substantially the same flow rate.

In some embodiments, each of the plurality of pumps may be configured to output a flow of gas at a fixed flow rate, and the method may further comprise enabling at least one of the plurality of pumps to provide a flow of gas from the enabled pumps to the outlet at the required flow rate.

In some embodiments, the method may further comprise outputting a flow of gas at the same fixed flow rate.

According to an aspect related to the third aspect, and applicable to any of the embodiments of the third aspect, there is provided a method of controlling an inflation apparatus for use with an inflation-based non-invasive blood pressure, NIBP, measurement apparatus, the inflation apparatus comprising an outlet configured to be coupled to a cuff of the inflation-based NIBP measurement apparatus; a plurality of pumps each configured to output a respective flow of gas to the outlet to produce a flow of gas at the outlet for inflating the cuff, the method in a control unit comprising (i) enabling at least one of the plurality of pumps to output a respective flow of gas to the outlet, wherein the number of pumps enabled by the control unit is based on a required flow rate of gas at the outlet for inflating the cuff, and/or (ii) controlling at least one of the plurality of pumps to output a respective flow of gas to the outlet at a respective flow rate, wherein the respective flow rate of the at least one of the plurality of pumps is controlled based on the required flow rate.

According to a fourth aspect, there is provided a computer program product comprising a computer readable medium having computer readable code embodied therein, the computer readable code being configured such that, on execution by a suitable computer, processor or control unit, the computer, processor or control unit is cause to perform the method according to the third aspect or the aspect related to the third aspect.

In some embodiments the suitable computer, processor or control unit is connected to, or is connectable to, the plurality of pumps.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF EMBODIMENTS

As described above, measuring the blood pressure (BP) of a subject during inflation of a cuff, rather than during deflation of the cuff from a peak pressure that is sufficient to prevent blood flower in the limb, allows the BP measurement to be completed more quickly, which helps to improve the comfort of the BP measurement for the subject. As part of this measurement process, the cuff should be inflated to the required pressure at a dedicated inflation rate, and the inflation apparatus described in the following provides a flexible solution relating to inflation-based BP measurements that is suitable for a large range of different cuff sizes and materials, without the need for complex adjustments to the pump or introduction of complicated control procedures. As is known, a cuff can be placed or wrapped around a part of a body of a subject and the cuff inflated to apply pressure to the body part underneath the cuff.

Figure 1:
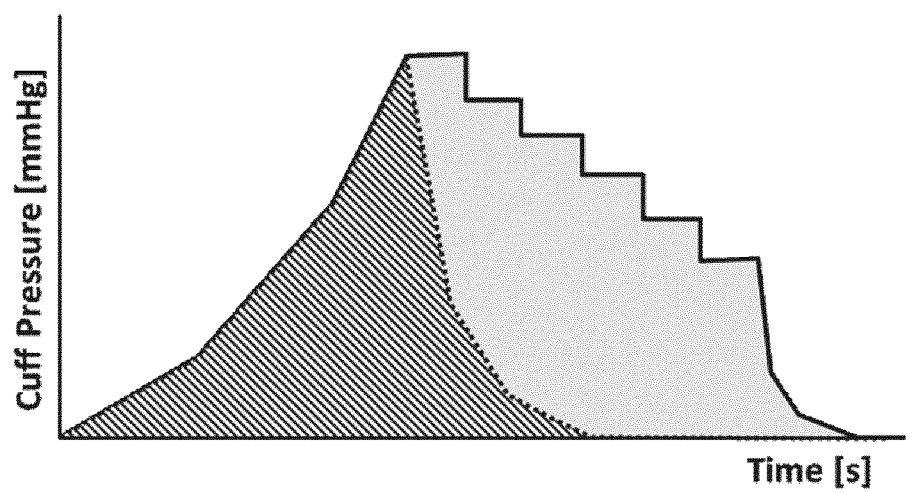
FIG. 1 is a graph of cuff pressure versus time measured for a conventional auscultatory or oscillometric NIBP measurement apparatus and for an inflation-based NIBP measurement apparatus.
Figure 2:
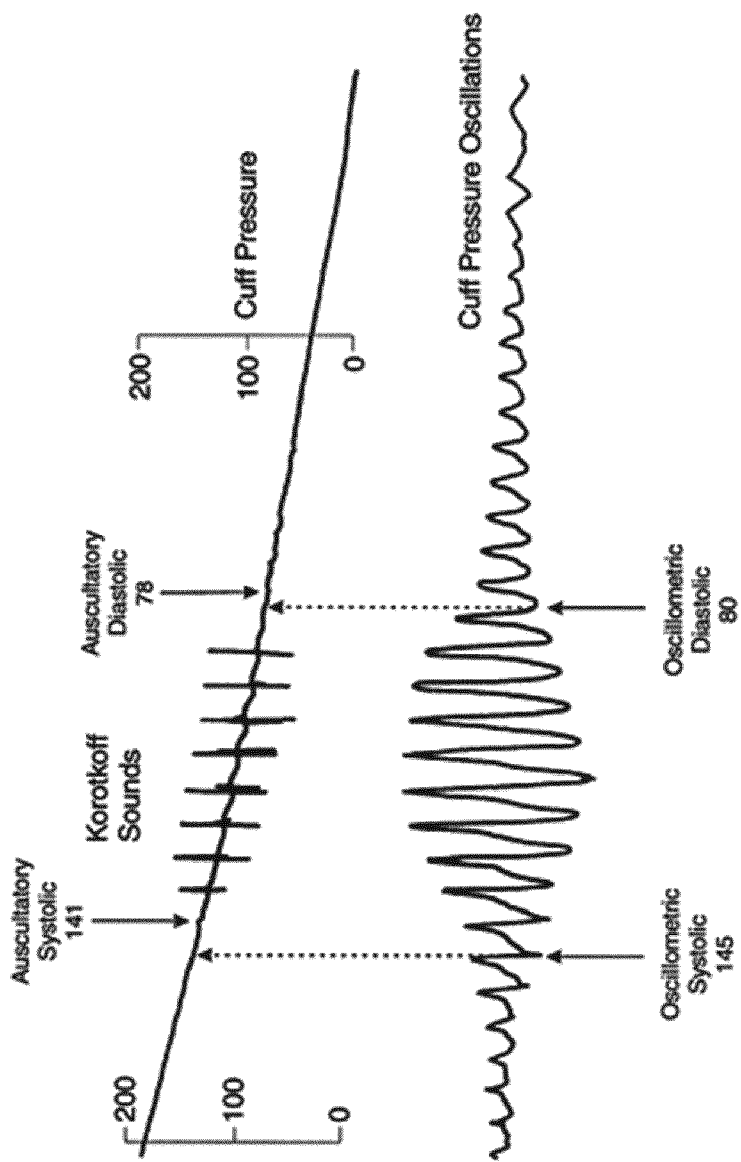
FIG. 2 is another graph of cuff pressure versus time for a conventional auscultatory or oscillometric NIBP measurement apparatus.
Figure 3:
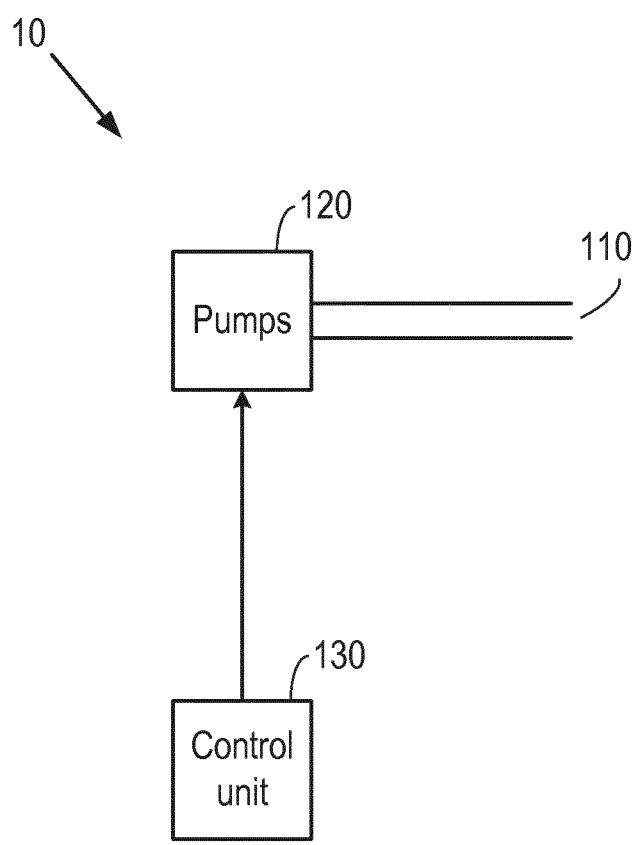
FIG. 3 is a diagram of an inflation apparatus according to an embodiment of the invention.

An inflation apparatus for use in or with an inflation-based non-invasive blood pressure (NIBP) measurement apparatus according to an embodiment of the invention is shown in FIG. 3. The inflation apparatus 10 is for providing a flow of gas to a cuff in the inflation-based NIBP measurement apparatus at a required or desired flow rate. The inflation apparatus 10 comprises an outlet 110 and a plurality of pumps 120. A control unit 130 is connected to the plurality of pumps 120 to control the operation of the plurality of pumps 120. The control unit 130 controls at least one of the plurality of pumps 120 to output a flow of gas (e.g. air) based on a required flow rate from the outlet 110.

The required flow rate may be determined based on at least one of a required rate of change of pressure in the cuff and a compliance value. The compliance value can be an overall compliance value that can be a combination of the compliance of the cuff, the compliance of the arm and of the wrapping of the cuff. The compliance of the cuff is defined as the rate of air flow into the cuff divided by the rate of pressure increase in the cuff. This overall compliance value is not constant, but depends on the pressure in the cuff. Thus the compliance value can be determined based on at least one of the pressure in the cuff, the size of the cuff, the elasticity of the material of the cuff, the compressibility of the tissue underneath the cuff, and the tightness of the wrapping of the cuff around the body part. The compliance value, and/or any of the factors which the determination of the compliance value may be based on, may be determined before or during inflation of the cuff. The required flow rate can be controlled using a feedback loop based on the desired rate of change of pressure and the actual rate of change of pressure.

The outlet 110 is configured to be coupled to an inflatable cuff of the inflation-based NIBP measurement apparatus. In some embodiments, the outlet 110 is configured such that it can be detachably coupled to cuffs having different sizes, for example a regular arm cuff, a neonatal cuff and a thigh cuff.

The plurality of pumps 120 are each configured to output a flow of gas (e.g. air) to the outlet 110. In some embodiments, each pump 120 in the plurality is configured to provide a flow of gas at a fixed output flow rate. That is, when each pump 120 is enabled (i.e. operated), the pump 120 provides a flow of gas at the fixed output flow rate (i.e. the flow rate of the pump 120 is not variable). In these embodiments, each of the pumps 120 in the plurality can output a flow of gas at the same fixed output flow rate, or substantially the same fixed output flow rate as the output flow rate may vary from pump to pump due to differences in tolerances and/or calibration etc. Alternatively, the pumps 120 in the plurality can output a flow of gas at a respective fixed output flow rate (i.e. one or more of the pumps 120 can have a different fixed output flow rate to the other pumps 120).

In alternative embodiments, at least one of the plurality of pumps 120 may be configured to output a flow of gas at a variable flow rate. That is, at least one of the plurality of pumps 120 can be configured to output the flow of gas at a flow rate selected from a range of flow rates at which the pump 120 can operate. Instead of a selection of flow rates, the flow rate can also be a continuous within the operating range. The output flow rate of the pump 120 can be controlled by the control unit 130. In some embodiments, each of the pumps 120 in the plurality may be configured to output a flow of gas at a variable flow rate. In these embodiments, each of the pumps 120 may have the same or substantially the same operating range of flow rates, or one or more of the pumps 120 may have a different operating range of flow rates to the other pumps 120. In some embodiments, the different operating ranges may overlap with some or all of each other, but in other embodiments the different operating ranges may be non-overlapping.

The control unit 130 is connected to the pumps 120 and controls the operation of the pumps 120 so that the pumps 120 provide a flow of gas at the outlet 110 at the required flow rate. Specifically the control unit 130 is configured to selectively enable and disable each of the pumps 120 (i.e. activate and deactivate) as required. In embodiments where one or more of the plurality of pumps 120 has a variable flow rate, the control unit 130 is configured to control the output flow rate of that pump 120 to an appropriate rate (e.g. via an appropriate control signal).

The control unit 130 can be implemented in numerous ways, with software and/or hardware, to perform the various functions described below. The control unit 130 may comprise one or more microprocessors or digital signal processor (DSPs) that may be programmed using software or computer program code to perform the required functions and/or to control components of the control unit 130 to effect the required functions. The control unit 130 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

In various implementations, the control unit 130 may be associated with or comprise one or more memory units (not shown) that comprise any type of memory, such as cache or system memory including volatile and non-volatile computer memory such as random access memory (RAM) static RAM (SRAM), dynamic RAM (DRAM), read-only memory (ROM), programmable ROM (PROM), erasable PROM (EPROM), and electrically erasable PROM (EEPROM). The control unit 130 or associated memory unit can also be used for storing program code that can be executed by a processor in the control unit 130 to perform the methods described herein.

In some specific embodiments that are described in more detail below, each of the plurality of pumps 120 is configured to output a flow of gas at a variable output flow rate, and the control unit 130 is configured to enable one or more of the pumps 120 to provide a flow of gas and to control a flow rate of the one or more enabled pumps 120 based on the required flow rate. For example, in some embodiments, the plurality of pumps 120 can comprise a first pump configured to output a flow of gas within a first range of flow rates and a second pump configured to output a flow of gas within a second range of flow rates, with the first range comprising higher flow rates than the second range. In some cases, the flow rates in the first range can be higher than the flow rates in the second range (i.e. so that the first range and second range do not overlap). The control unit 130 can enable one or both of pump 120 and pump 120 and control the output flow rate to provide a flow of gas from the enabled pump 120 or pumps 120 to the outlet 110 at the required flow rate. An exemplary implementation of these embodiments is described in relation to FIGS. 4 and 5.

In other embodiments, each of the plurality of pumps 120 is configured to output a flow of gas at a respective fixed output flow rate (where the respective fixed output flow rates can be the same, or substantially the same, or different), and the control unit 130 is configured to enable at least one of the plurality of pumps 120 to provide a flow of gas from the enabled pumps 120 to the outlet at the required flow rate. For example, in some embodiments, the plurality of pumps 120 may each be configured to have a same or substantially the same fixed flow rate, and the control unit 130 may be configured to determine how many of the plurality of the pumps 120 to enable in order to achieve the required flow rate. An exemplary implementation of these embodiments is described in relation to FIG. 5.

It will be appreciated that FIG. 3 only shows the components required to illustrate this aspect of the invention, and in a practical implementation the inflation apparatus 10 may comprise additional components to those shown. For example, the inflation apparatus 10 may comprise one or more valves for safety reasons, a battery or other power supply for powering the plurality of pumps 120 and control unit 130, a memory module for storing program code, and/or one or more interface components that allow a user (e.g. the subject or healthcare professional) to interact with and control the inflation apparatus 10.

Figure 4:
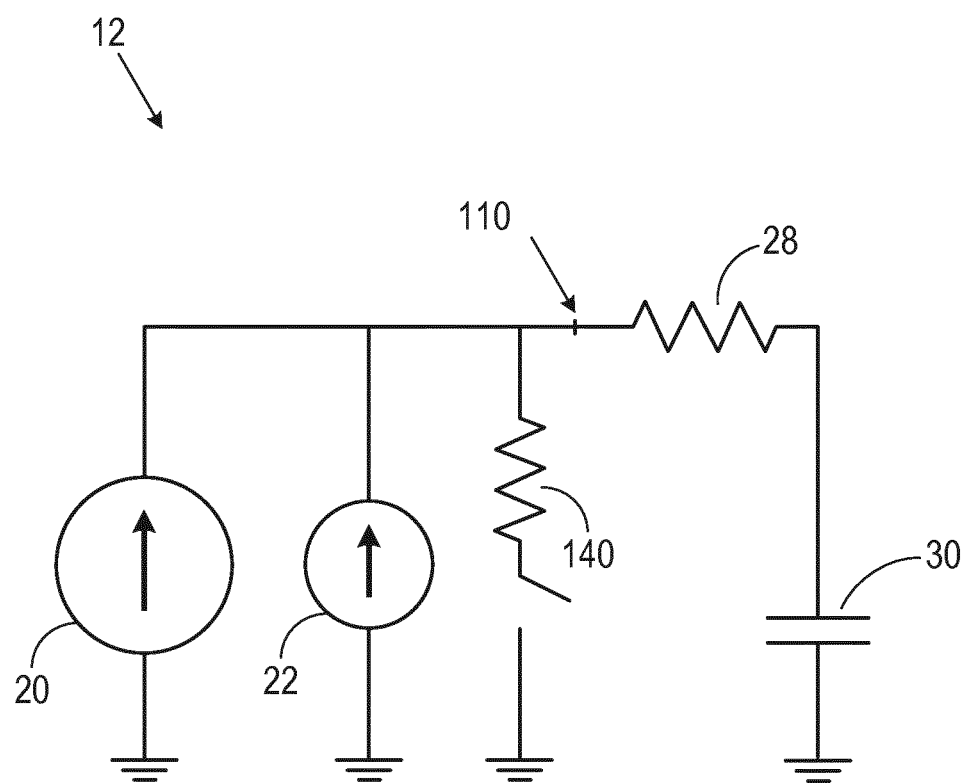
FIG. 4 shows a circuit diagram representation of an implementation of the inflation apparatus according to an embodiment of the invention in an inflation-based NIBP measurement apparatus.

FIG. 4 is a circuit diagram representation of an implementation of an inflation apparatus according to an embodiment of the invention in an inflation-based NIBP measurement apparatus. In this embodiment the plurality of pumps 120 comprises a first pump 20 and a second pump 22. The layout of the implementation of the inflation-based NIBP measurement apparatus 12 is shown as a circuit diagram comprising connections between an outlet 110, the first pump 20 and the second pump 22 forming the inflation apparatus, and a release valve 140. In operation the outlet 110 is connected to a tube 28, and the tube 28 is connected to a cuff 30 so as to allow gas to pass through from the first pump 20 and/or the second pump 22 to the cuff 30 (depending on which of the first pump 20 and the second pump 22 are enabled), which is inflatable. A release valve 140 is connected to the cuff 30 (not shown) and/or tube 28 and to the atmosphere so as to allow deflation of the cuff 30 after a blood pressure measurement has been completed. It will be appreciated that the relative arrangements of the outlet 110 and the release valve 140 shown in FIG. 4 is exemplary and they can be arranged differently to that shown (e.g. the release valve 140 can be located on the side of the cuff 30 with respect to the outlet 110 rather than being located on the side of the first pump 20 and the second pump 22).

In the circuit diagram, the release valve 140 is modelled as a resistor connected to ground (e.g. the atmosphere) via a switch (i.e. the release valve allows a flow of gas there through when the switch is closed), the tube 28 is modelled as a resistor (since it provides some resistance to the flow of gas based on the dimensions of the tube 28), the cuff 30 is modelled as a capacitor (as it stores air or gas), and the first and second pumps 20, 22 are modelled as respective current sources (as they provide air or gas into the circuit).

In this embodiment, the first pump 20 is a pump that can provide a relatively large maximum flow rate of gas (e.g. 2-70 mL/s) and the second pump 22 is a pump that can provide a flow of gas in a low flow range (e.g. 0-3 mL/s). The first pump 20 may be a diaphragm pump and the second pump 22 may be a piezo pump, although those skilled in the art will appreciate that other types of pump can be used. The first pump 20 is configured to output a flow of gas within a first range of flow rates and the second pump 22 is configured to output a flow of gas within a second range of flow rates. As the first pump 20 is larger than the second pump 22, the first range comprises higher flow rates than the second range. In some embodiments, the flow rates in the first range are higher than the flow rates in the second range (i.e. the ranges do not overlap). Which of the first and second pumps 20, 22 is enabled, and the flow rates of the first pump 20 and the second pump 22 is controlled by a control unit (not shown in FIG. 4) at the inflation apparatus or a processor/control unit at an inflation-based NIBP measurement apparatus 12. The control unit or processor may be configured to receive at least one of a rate of change of pressure in the cuff 30 and a compliance value. This information may be received through a communication module (not shown in FIG. 4) at the inflation-based NIPB measurement apparatus 12 from an external device, or input by a user of the inflation-based NIPB measurement apparatus 12. The control unit or processor may be further configured to determine the required flow rate based on the received at least one of the rate of change of pressure in the cuff 30 and the compliance value, and to control the operation of at least one of the first pump 20 and the second pump 22 accordingly.

If the required flow rate is within the first range, i.e. within the operable range of the first pump 20, the control unit 130 enables the first pump 20 and controls the flow rate of the first pump 20 so as to output a flow of gas at the required flow rate. In this case the second pump 22 will be disabled or deactivated so that it does not output a flow of gas. Similarly, if the required flow rate is within the second range, i.e. within the operable range of the second pump 22, the control unit 130 enables the second pump 22 and controls the flow rate of the second pump 22 so as to output a flow of gas at the required flow rate. In this case the first pump 20 will be disabled or deactivated so that it does not output a flow of gas. In some cases, if the required flow rate is higher than a maximum operable flow rate of the first pump 20, the control unit 130 can enable both the first pump 20 and the second pump 22 so that both pumps output a flow of gas at their respective flow rates (i.e. a combination of a flow of gas from the first pump 20 and a flow of gas from the second pump 22) to form a combined flow of gas at the outlet 110.

In some embodiments, which can be useful where it is not possible to finely control the output flow rate of the first pump 20 (e.g. where the output flow rate can only change in steps rather than being adjusted smoothly), if the required flow rate is in the first range but is not equal to one of the flow rates that can be output by the first pump 20, then the control unit can enable the first pump 20 and control the first pump 20 to output gas at a flow rate below the required flow rate, and enable the second pump 22 and control the second pump 22 to output gas at a flow rate so that the combined flow of gas from the first pump 20 and the second pump 22 is at or near the required flow rate.

Therefore, in this embodiment, a standard higher-flow pump and a standard lower-flow pump can be used to increase the overall flow range of the inflation-based NIPB measurement apparatus 12 to allow the inflation apparatus to be coupled to a large range of different-sized cuffs. For larger cuffs such as a thigh cuff, the first pump 20 can be used (in some cases together with the second pump 22) to output relatively high flow rates to inflate the cuff at a suitable and reasonable rate. For smaller cuffs such as a neonatal cuff, the second pump 22 can be used (and the first pump 20 deactivated or disabled) to output a low flow rate to inflate the cuff 30 at the required pressure change rate and reduce the risk of damaging the cuff.

Also, in some embodiments the enabling or disabling of the first pump 20 and the second pump 22 can be performed gradually so as to avoid inducing artefacts which may interfere with the measurement of blood pressure.

As the cuff 30 is being inflated by the pump(s) 20, 22, a blood pressure measurement can be made using measurements from a sensor in the inflation-based NIBP measurement apparatus 12. The sensor is configured to measure arterial oscillations in the body part of the subject as the cuff 30 is being inflated. This sensor may be a pressure sensor configured to measure changes in cuff pressure resulting from pulsation of the arterial blood in the arteries under the cuff. In some embodiments, the sensor may comprise a pulse rate sensor configured to measure the pulse rate of the subject during the inflation. In some embodiments, the sensor may comprise a photoplethysmography (PPG) sensor, and accelerometer, or an electrocardiogram (ECG) sensor, although those skilled in the art will be ware of other types of heart rate sensor can be used, such as a camera, a radar, an impedance cardiogram, a heart sound sensor, etc. In use, the sensor may be attached to or otherwise in contact with the appropriate part of the body of the subject in order to measure arterial oscillations. In some embodiments, the sensor may be integrated with the cuff so that the subject or healthcare professional only has to wrap or place the cuff around the body part in order to start using the inflation-based NIBP measurement apparatus 12.

Once the sensor has completed sufficient arterial oscillation measurements for a BP measurement to be obtained, the release valve 140 can be opened so as to quickly release the pressure in the inflatable cuff 30 to minimize any discomfort caused to the subject.

The arterial oscillations measured by the sensor are then received at the control unit of the inflation apparatus or processing/control unit of the inflation-based NIBP measurement apparatus 12, which is then configured to determine the blood pressure of the subject based on the received arterial oscillations measurements. For example, in some embodiments where the sensor comprises an accelerometer, the control unit or the processing unit may be configured to process acceleration signals from the accelerometer to extract the movements caused by the beating of the heart/pulses of blood in the circulatory system. In some embodiments, there can be a wired connection between the sensor and the control unit or the processing unit, whereas in other embodiments, the sensor can communicate with the control unit or the processing unit wirelessly.

Figure 5:
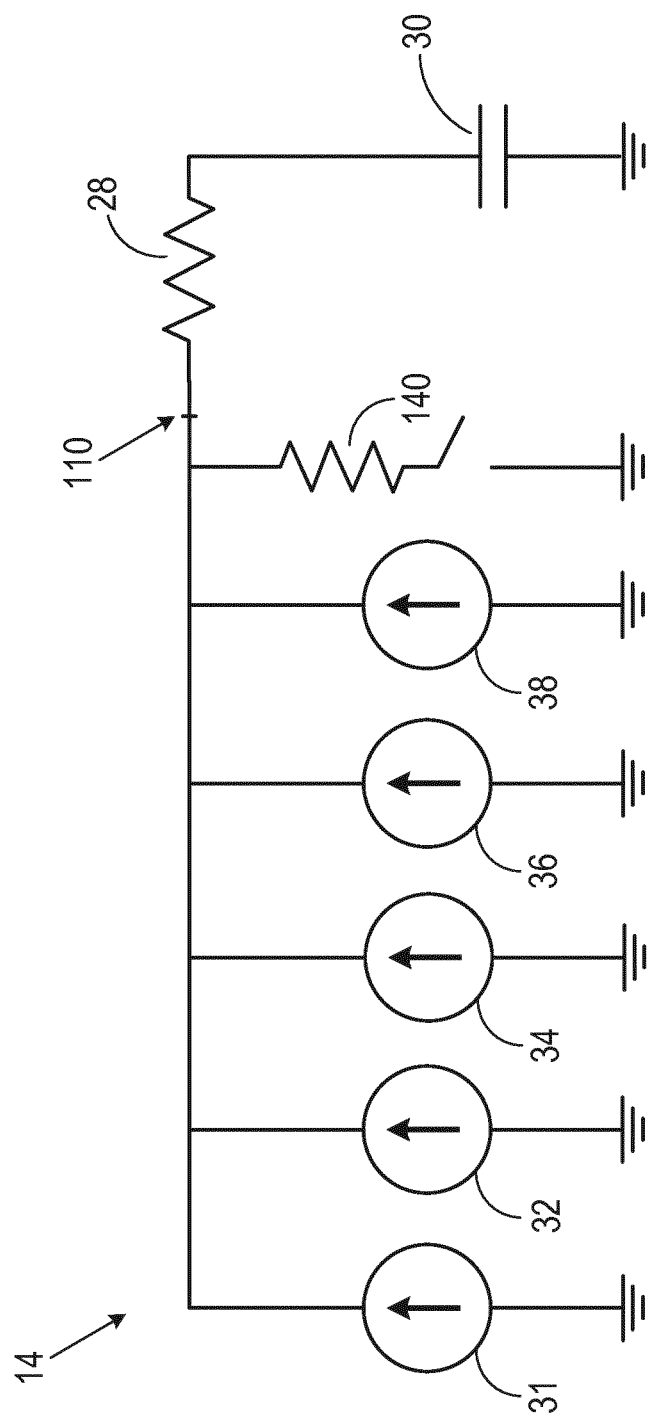
FIG. 5 shows a circuit diagram representation of an implementation of the inflation apparatus according to another embodiment of the invention in an inflation-based NIBP measurement apparatus.

FIG. 5 is a circuit diagram representation of an implementation of an inflation apparatus according to another embodiment of the invention in an inflation-based NIBP measurement apparatus. The layout of the implementation of the inflation-based NIBP measurement apparatus 14 is shown as a circuit diagram comprising connections between an outlet 110 and a plurality of pumps 31, 32, 34, 36, 38 forming the inflation apparatus, and a release valve 140. In operation the outlet 110 is connected to a tube 28 and the tube 28 is connected to a cuff 30 so as to allow gas to pass through from the plurality of pumps 31, 32, 34, 36, 38 (depending on which of the pumps are enabled) to the cuff 30. The release valve 140 is connected to the cuff 30 (not shown) and/or tube 28 and to the atmosphere so as to allow deflation of the cuff 30 after a blood pressure measurement has been completed. It will be appreciated that although FIG. 5 shows five pumps, an inflation apparatus can have more or less than five pumps.

In the circuit diagram, the release valve 140 is modelled as a resistor connected to ground (e.g. the atmosphere) via a switch (i.e. the release valve allows a flow of gas there through when the switch is closed), the tube 28 is modelled as a resistor (since it provides some resistance to the flow of gas based on the dimensions of the tube 28), the cuff 30 is modelled as a capacitor (as it stores air or gas), and the pumps 31, 32, 34, 36, 38 are modelled as respective current sources (as they provide air or gas into the circuit).

Each of the plurality of pumps 31, 32, 34, 36, 38 can be a piezo pump, although it will be appreciated that other types of pump can be used. In some cases each of the pumps is of the same type, but in other cases one or more of the pumps can be different to the others.

In a first set of embodiments relating to FIG. 5, the plurality of pumps 31, 32, 34, 36, 38 are configured to output a flow of gas at a same fixed flow rate, or at a substantially same flow rate since the output flow may vary from pump to pump due to differences in tolerances and/or calibration, etc. For example, for high flow piezo pumps the same fixed flow rate may be around 4 mL/s. Each of the plurality of pumps 31, 32, 34, 36, 38 can be enabled individually, based on a required flow rate, by the control unit (not shown in FIG. 5) at the inflation apparatus or a processor/control unit at the inflation-based NIBP measurement apparatus 14. The control unit or processor may be configured to receive at least one of a rate of change of pressure in the cuff 30 and a compliance value. This information may be received through a communication module (not shown in FIG. 5) at the inflation apparatus from an external device, or input by a user of the inflation-based NIBP apparatus 14. The control unit or processor may be further configured to determine the required flow rate based on the received at least one of the rate of change of pressure in the cuff 30 and the compliance value, and to enable at least one of the plurality of pumps 31, 32, 34, 36, 38 accordingly. For example, if a flow rate of 40 mL/s is required for the blood pressure measurement, ten of the above-mentioned high flow piezo pumps would need to be enabled to achieve this flow rate.

Since each of the plurality of pumps 31, 32, 34, 36, 38 is configured to output a flow of gas at the same or substantially the same flow rate in this embodiment, the control unit can determine how many of the plurality of pumps 31, 32, 34, 36, 38 to enable to provide a flow of gas from the enabled pumps to the outlet 110 at the required flow rate, and the control unit can then enable that number of pumps. For example the control unit can determine the number N of required pumps by dividing the required flow rate R by the fixed output flow rate F of a single pump. It will be appreciated that each of the plurality of pumps 31, 32, 34, 36, 38 can be configured to have a relatively low fixed flow rate so as to accommodate lower required flow rates, although this requires a large number of pumps in order to achieve relatively high required flow rates. It will also be appreciated that in this set of embodiments the resolution of the flow rate provided to the outlet 110 will depend on the number of pumps in the inflation apparatus and the fixed output flow rate of each pump.

Therefore, in this embodiment, a plurality of standard pumps can be used while allowing the inflation apparatus to be coupled to a large range of different-sized cuffs. For larger cuffs such as a thigh cuff, more pumps can be enabled so as to collectively output a relatively high flow rate at the outlet 110 to inflate the cuff at a suitable and reasonable rate. For smaller cuffs such as a neonatal cuff, fewer pumps can be enabled (e.g. one) to output a relatively low flow rate to inflate the cuff 30 at the required pressure change rate and reduce the risk of damaging the cuff.

Once the inflation of the cuff 30 and the blood pressure measurements performed during the inflation of the cuff 30 are completed (which can be as described above with reference to FIG. 4), the release valve 140 can be opened so as to release the pressure in the cuff 30 in a quick manner to minimize the discomfort caused to the subject.

Although it is described above that each of the plurality of pumps 31, 32, 34, 36, 38 is configured to output a flow of gas at the same or substantially the same fixed flow rate, in another set of embodiments each of the plurality of pumps 31, 32, 34, 36, 38 may be configured to output a flow of gas at a flow rate in a range of flow rates (i.e. the output flow rate of each pump is variable). Each of the plurality of pumps 31, 32, 34, 36, 38 can be enabled individually and the respective output flow rate controlled by the control unit (not shown in FIG. 5) at the inflation apparatus or a processor/control unit at the inflation-based NIBP measurement apparatus 14, based on a required flow rate. In some embodiments, the control unit enables all of the pumps 31, 32, 34, 36, 38 and controls each pump 31, 32, 34, 36, 38 to provide a flow of gas at the same or substantially the same flow rate (e.g. by providing the same control signal to each pump 31, 32, 34, 36, 38). The control unit therefore controls the output flow rate of all of the pumps 31, 32, 34, 36, 38 together to produce a flow of gas at the outlet 110 at the required rate. As with the first set of embodiments above, it will be appreciated that each of the plurality of pumps 31, 32, 34, 36, 38 can be configured to have a relatively low fixed flow rate so as to accommodate lower required flow rates, but this requires a large number of pumps in order to achieve relatively high required flow rates. It will also be appreciated that in this set of embodiments the resolution of the flow rate provided to the outlet 110 will depend on the number of pumps in the inflation apparatus and the step-size of the output flow rate of each pump. It will also be appreciated that in this set of embodiments the resolution of the flow rate provided to the outlet 110 will depend on the number of pumps in the inflation apparatus and the fixed output flow rate of each pump.

Figure 6:
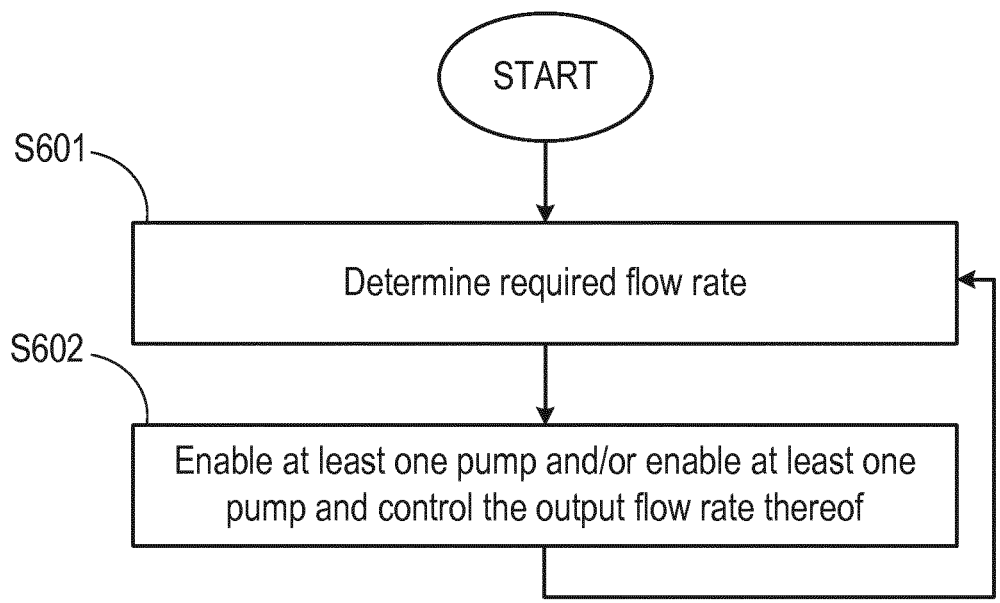
FIG. 6 is a flow chart illustrating an exemplary method for operating an inflation apparatus according to a general embodiment of the invention.

The flow chart in FIG. 6 illustrates an exemplary method for controlling an inflation apparatus for use in an inflation-based NIBP measurement apparatus. This method can be implemented by an inflation apparatus as shown in any of FIGS. 3-5. It will be appreciated that in some embodiments the inflation apparatus 10 can comprise computer program code for enabling the control unit 130 to perform the method.

In the first step S601, which is optional, a required flow rate for a cuff can be determined. This required flow rate may be preset for a particular cuff, but in other embodiments it can be determined based on at least one of a rate of change of pressure for the cuff and a compliance value. This information (whether the required flow rate, the rate of change of pressure for the cuff and/or the compliance value) may be received at the control unit 130 of the inflation apparatus 10 from an external device, such as a remote computer or a remote memory, or be input by a user of the apparatus.

In step S602, the control unit 130 determines which of the plurality of pumps in the inflation apparatus to enable based on the required flow rate and, where the output flow rate of the pumps is variable, the flow rate required from the enabled pumps, and then enables and/or controls the pumps accordingly to provide a flow of gas to the outlet at the required flow rate.

Thus, where the pumps are configured to output a flow of gas at a fixed flow rate (i.e. the flow rates of the pumps are not variable), step 602 can comprise enabling a required number of the pumps to provide a combined flow of gas at the outlet of the inflation apparatus at the required flow rate. In these embodiments, the method can comprise determining the number of pumps to enable by dividing the required flow rate by the fixed flow rate of an individual pump so as to determine a number of pumps to enable to collectively achieve the required flow rate.

In other embodiments where the plurality of pumps are each configured to output a flow of gas at a variable flow rate, step 602 can comprise determining which one or more pumps to enable and the flow rate required in order for the enabled pumps to collectively achieve the required flow rate, and enabling that or those pumps at the determined flow rates.

In some embodiments as the required flow rate will change over time (as the compliance changes as a function of pressure), steps S601 and S602 may be performed repeatedly in the manner of a feedback loop to adjust the flow rate provided by the pumps to the required flow rate.

Figure 7:
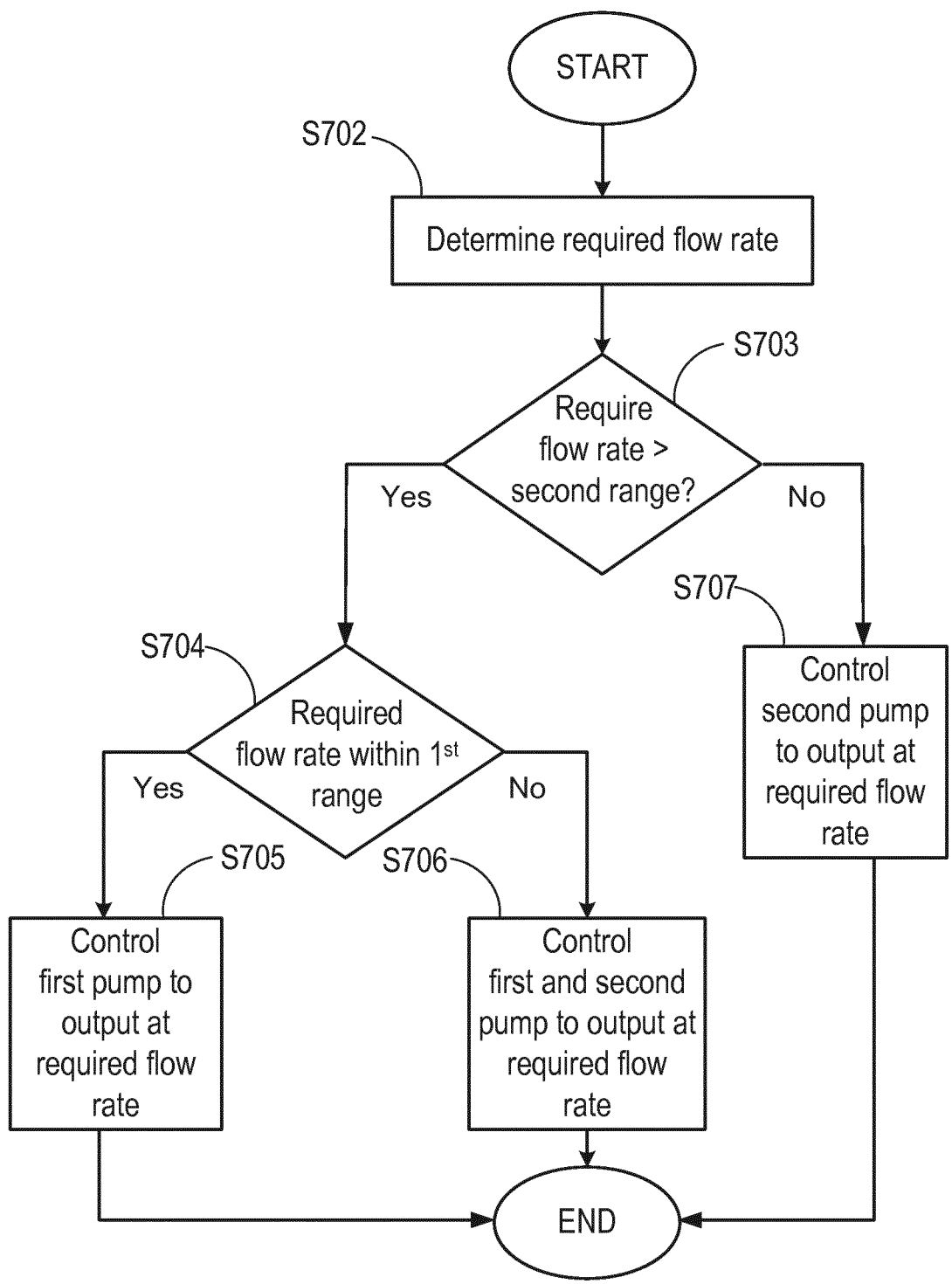
FIG. 7 is a flow chart illustrating another exemplary method for operating an inflation apparatus according to the embodiment shown in FIG. 4.

The flow chart in FIG. 7 illustrates an exemplary method for controlling an inflation apparatus for use with an inflation-based NIBP measurement apparatus according to the specific embodiment of the inflation apparatus shown in FIG. 4. Thus, this method can be implemented by an inflation apparatus as shown in FIG. 4, which comprises a first pump and a second pump, with the first pump being configured to output a flow of gas within a first range of flow rates and the second pump being configured to output a flow of gas within a second range of flow rates, and the first range comprising higher flow rates than the second range. It will be appreciated that in some embodiments the inflation apparatus 10 can comprise computer program code for enabling the control unit 130 to perform the method.

In the first step S702, a required flow rate for a cuff can be determined. This required flow rate may be preset for a particular cuff, but in other embodiments it can be determined based on at least one of a rate of change of pressure for the cuff and a compliance value. This information (whether the required flow rate, the rate of change of pressure for the cuff and/or the compliance value) may be received at the control unit 130 of the inflation apparatus 10 from an external device, such as a remote computer or a remote memory, or be input by a user of the apparatus.

In step S703, the control unit 130 determines whether the required flow rate is larger than the flow rates in the second range (i.e. larger than the flow rates that the second pump can generate). If it is determined that the required flow rate is higher than the flow rates in the second range, the method proceeds to step S704. Otherwise, i.e. if it is determined that the required flow rate is not higher than the flow rates in the second range, the method proceeds to step S707.

In step S704, the control unit 130 determines whether the required flow rate is within the first range (i.e. within the range of flow rates that can be generated by the first pump). If it is determined that the required flow rate is within the first range, the method proceeds to step S705 in which the control unit 130 controls the first pump to output a flow of gas at the required flow rate. Otherwise, if it is determined that the required flow rate is not within the first range, the control unit 130 controls the first pump and the second pump so as to collectively output a flow of gas at the required flow rate in step S706 (i.e. both the first pump and second pump are enabled), if this is possible (i.e. if a combined output flow rate from the first pump and the second pump can equal the required flow rate), and otherwise controls the first pump and the second pump to output a respective flow of gas to the outlet at their respective maximum flow rates.

In step S707, the control unit 130 controls the second pump to output a flow of gas at the required flow rate.

In some embodiments as the required flow rate will change over time (as the compliance changes as a function of pressure), the method in FIG. 7 may be performed repeatedly in the manner of a feedback loop to adjust the flow rate provided by the pumps to the required flow rate.

Thus, in this particular method, the required flow rate into the inflatable cuff of the inflation-based NIBP measurement apparatus is achieved by enabling at least one of the first pump and the second pump and controlling a flow rate of the enabled pump(s).

There is therefore provided an inflation apparatus for an inflation-based NIBP measurement apparatus and a method of operating the same that allows a cuff to be inflated according to a desired flow rate so as to suit a large range of different cuff sizes and materials and/or to prevent inducing oscillation artefacts, without having to modify the components of the pump or to implement intricate control techniques. Furthermore, since more than one pumps are provided at the inflation apparatus, problems relating to pump stalling can be circumvented by for example enabling other pumps in the apparatus until the defective pump is fixed.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An inflation apparatus for use in an inflation-based non-invasive blood pressure (NIBP) measurement apparatus, the inflation apparatus comprising: an outlet configured to be coupled to a cuff of the inflation-based NIBP measurement apparatus; a plurality of pumps each configured to output a respective flow of gas to the outlet to produce a flow of gas at the outlet for inflating the cuff; and a control unit comprising a processor and configured to: (i) enable at least one of the plurality of pumps to output a respective flow of gas to the outlet, wherein a number of the plurality of pumps enabled by the control unit is based on a required flow rate of gas at the outlet for inflating the cuff, and/or (ii) control at least one of the plurality of pumps to output a respective flow of gas to the outlet at a respective flow rate, wherein the respective flow rate of the at least one of the plurality of pumps is controlled based on the required flow rate, wherein the required flow rate is determined based on at least one of a required rate of change of pressure in the cuff and a compliance value of the cuff.

2. The inflation apparatus according to claim 1, wherein the plurality of pumps comprises a first pump configured to output a respective flow of gas within a first range of flow rates and a second pump configured to output a respective flow of gas within a second range of flow rates, wherein the first range comprises higher flow rates than the second range, and wherein the control unit is configured to enable one or both of the first pump and the second pump to provide a flow of gas at the outlet at the required flow rate.

3. The inflation apparatus according to claim 2, wherein enabling and/or disabling of at least one of the first pump and the second pump is performed gradually.

4. The inflation apparatus according to claim 2, wherein the first pump is a diaphragm pump and the second pump is a piezo pump.

5. The inflation apparatus according to claim 1, wherein each of the plurality of pumps is configured to output gas in a range of flow rates, and the control unit is configured to enable at least one of the plurality of pumps to output a respective flow of gas and to control the respective flow rate of the at least one of the plurality of pumps to provide a respective flow of gas to the outlet at the required flow rate.

6. The inflation apparatus according to claim 5, wherein the control unit is configured to enable each of the plurality of pumps to provide a respective flow of gas to the outlet.

7. The inflation apparatus according to claim 5, wherein the control unit is configured to control each of the enabled pumps to output a respective flow of gas at the same or substantially the same flow rate.

8. The inflation apparatus according to claim 1, wherein each of the plurality of pumps is configured to output a respective flow of gas at a fixed flow rate, and the control unit is configured to enable at least one of the plurality of pumps to provide a flow of gas from the enabled pumps at the outlet at the required flow rate.

9. The inflation apparatus according to claim 8, wherein each of the plurality of pumps output a respective flow of gas at the same or substantially the same fixed flow rate.

10. An inflation-based non-invasive blood pressure (NIBP) measurement apparatus comprising:
the inflation apparatus as claimed in claim 1; and
a sensor configured to measure arterial oscillations in a body part of a subject when, in operation, an inflatable cuff is positioned around the body part, with the cuff being coupled to the outlet of the inflation apparatus and being inflated by the inflation apparatus, wherein the control unit of the inflation apparatus or a processing unit in the inflation-based NIBP measurement apparatus is configured to receive measurements of arterial oscillations from the sensor and to determine the blood pressure of the subject based on the received measurements.

11. The inflation-based NIBP measurement apparatus according to claim 10, further comprising a release valve connected to the inflatable cuff for selectively deflating the cuff.

12. The inflation-based NIBP measurement apparatus according to claim 10, wherein the plurality of pumps comprises a first pump configured to output a respective flow of gas within a first range of flow rates and a second pump configured to output a respective flow of gas within a second range of flow rates, wherein the first range comprises higher flow rates than the second range, and wherein the control unit is configured to enable one or both of the first pump and the second pump to provide a flow of gas at the outlet at the required flow rate.

13. The inflation-based NIBP measurement apparatus according to claim 12, wherein enabling and/or disabling of at least one of the first pump and the second pump is performed gradually.

14. The inflation-based NIBP measurement apparatus according to claim 12, wherein the first pump is a diaphragm pump and the second pump is a piezo pump.

15. The inflation-based NIBP measurement apparatus according to claim 10, wherein each of the plurality of pumps is configured to output gas in a range of flow rates, and the control unit is configured to enable at least one of the plurality of pumps to output a respective flow of gas and to control the respective flow rate of the at least one of the plurality of pumps to provide a respective flow of gas to the outlet at the required flow rate.

16. The inflation-based NIBP measurement apparatus according to claim 15, wherein the control unit is configured to enable each of the plurality of pumps to provide a respective flow of gas to the outlet.

17. A method of controlling an inflation apparatus for use with an inflation-based non-invasive blood pressure (NIBP) measurement apparatus, the inflation apparatus comprising an outlet configured to be coupled to a cuff of the inflation-based NIBP measurement apparatus; a plurality of pumps each configured to output a respective flow of gas to the outlet to produce a flow of gas at the outlet for inflating the cuff, the method adapted to be executed by a control unit comprising a processor, comprising: (i) enabling at least one of the plurality of pumps to output a respective flow of gas to the outlet, wherein a number of the plurality of pumps enabled by the control unit is based on a required flow rate of gas at the outlet for inflating the cuff, and/or (ii) controlling at least one of the plurality of pumps to output a respective flow of gas to the outlet at a respective flow rate, wherein the respective flow rate of the at least one of the plurality of pumps is controlled based on the required flow rate, wherein the required flow rate is determined based on at least one of a rate of change of pressure at the cuff and a compliance value of the cuff.

18. A non-transitory computer program product comprising a computer readable medium having computer readable code embodied therein, the computer readable code being configured such that, on execution by a computer, processor or control unit, the computer, processor or control unit is caused to perform the method of claim 17.

\* \* \* \* \*